United States Patent [19]

Samelson

[11] 4,304,227

[45] Dec. 8, 1981

[54] DEVICE FOR TREATMENT OF SNORING, BRUXISM OR FOR AVOIDANCE OF SLEEP APNEA

[76] Inventor: Charles F. Samelson, 5712 S. Kenwood, Chicago, Ill. 60637

[21] Appl. No.: 69,890

[22] Filed: Aug. 27, 1979

Related U.S. Application Data

[63] Continuation-in-part of Ser. No. 883,270, Mar. 3, 1978, Pat. No. 4,169,473.

[51] Int. Cl.$^3$ .............................................. A61F 5/56
[52] U.S. Cl. .................................. 128/136; 128/132 R
[58] Field of Search ........... 128/136, 137, 138, 132 R, 128/15, 206.21

[56] References Cited

U.S. PATENT DOCUMENTS

| | | | |
|---|---|---|---|
| 3,211,143 | 10/1965 | Grossberg | 128/136 |
| 3,448,738 | 6/1969 | Berghash | 128/136 |
| 3,692,205 | 9/1972 | Greenberg | 128/136 |
| 4,169,473 | 10/1979 | Samelson | 128/136 |
| 4,196,724 | 4/1980 | Wirt et al. | 128/136 |

FOREIGN PATENT DOCUMENTS

| | | | |
|---|---|---|---|
| 65194 | 11/1892 | Fed. Rep. of Germany | 128/136 |
| 2704709 | 8/1977 | Fed. Rep. of Germany | 128/136 |

Primary Examiner—Henry J. Recla
Attorney, Agent, or Firm—Norman Lettvin

[57] ABSTRACT

A device is provided for positioning within the mouth of a user for preventing snoring and nocturnal tooth grinding. The device is an integrally molded body. The device provides dental engaging portions and a rearwardly-opening central socket for cooperating with the forward portion of the user's tongue in a manner to draw the tongue forwardly so as to increase the unobstructed dimension of the nasal breathing passage. When operatively positioned within the mouth, some of the user's upper and lower teeth will enter into recesses provided by the device. The device substantially eliminates oral breathing. The tongue will be held in the socket by a negative pressure developed in the socket. When the tongue is held, it draws the body of the tongue forwardly of its usual restive position behind the lower teeth and adjacent the soft palate, the uvula and the posterior pharyngeal wall, thereby increasing the dimension of the air flow passage through the nasopharynx to facilitate nasal breathing. The device's engagement with at least portions of one of the user's dental arches operates to eliminate nocturnal toothgrinding.

6 Claims, 7 Drawing Figures

DEVICE FOR TREATMENT OF SNORING, BRUXISM OR FOR AVOIDANCE OF SLEEP APNEA

This application is a continuation-in-part of a copending application, Ser. No. 883,270, filed Mar. 3, 1978 now issued as U.S. Pat. No. 4,169,473 dated Oct. 2, 1979.

This invention relates to an anti-snore and anti-toothgrinding device, and more particularly, to a device for selective insertion within the mouth of a user so as to obstruct the oral flow of air past the lips of the user, and to increase the size of the air passageway through the oro- and naso-pharynx, and which may also be provided with means for immobilizing jaw movement.

BACKGROUND OF THE INVENTION

Snoring is caused by the relaxation of body tissue in the lingual compartment, the tissue including the tongue, the pharyngeal folds, the soft palate, the muscularis uvulae and the palate-pharyngeal arch. During normal waking hours, muscle tone in most individuals unconsciously maintains the above structures in adequate spacial relationships so as not to interfere with the free passage of air therepast. However, with increasing age, and during periods of unconsciousness, some muscle tone is lost, thereby allowing one or more of the tongue, the pharyngeal folds, the soft palate, the uvulae and the posterior pharyngeal wall to vibrate as tidal air flows therepast.

While the act of snoring is socially discomfitting to other persons who hear the snores, and especially annoying to a spouse attempting to sleep, it can also cause harmful complications to the snorer, such as disturbed rest, excessive drying of the oro- and naso-pharyngeal mucous membranes with consequent injury to the throat, middle and inner ear, susceptibility to infection, vertigo and impaired hearing. Of equal importance is the fact that people who snore are not making use of the physiologically beneficial aspects of nasal breathing. The anatomical nasal structures (such as the turbinates, mucous membranes, etc.) provide moistening and cleansing functions during sleep.

Prior patents, such as U.S. Pat. No. 3,132,647, have dealt with the various lingual compartment tissues and their relationship to the snoring phenomenon. Such patients disclose that snoring should and can be reduced, if not altogether prevented, by providing for unobstructed air flow between the tongue and the soft palate. U.S. Pat. No. 3,132,647 seeks to keep the passage open by engaging and depressing the rear portion of the tongue while supporting a portion of the downwardly-hanging soft palate. Oral breathing is permitted, and no attempt is made to prevent vibration of the forward end of the tongue.

Other patented devices have been proposed as "snore-preventing" such as U.S. Pat. Nos. 1,774,446 and 3,434,470, and British Pat. No. 1,248,474. All such prior proposals have been constructed to permit, or at least allow, the partial inhalation of air orally to insure that oral breathing occurred.

While U.S. Pat. No. 2,867,212 recognizes that snoring is caused by vibrations of the soft palate and uvula and could be prevented if oral breathing is prevented, the mouthpiece described in said patent is intended to serve as an aid for practice of nasal breathing by blocking the oral flow of air. No attempt is made in said device to open the naso-pharynx, thus presenting a troublesome situation for users whose muscle tone is such as to partially close the nasal passageway.

British Pat. No. 751,381 includes a device to be held within the mouth of a user, said device having a central open bore provided for continuous passage of air.

It is one object of the present invention to provide an anti-snore device which serves to receive and hold the forward portion of the tongue in a forward position, thereby drawing the remainder of the tongue forwardly and in such a way that no portion of the tongue, or other oral soft tissue, will vibrate during breathing.

It is a further object of the present invention to provide an anti-snore device which not only holds the forward portion of the tongue forwardly but also prevents oral breathing by obstructing the flow of air through the mouth.

It is another object of this invention to provide an anti-snore device which not only prevents oral breathing, but also, opens the internal air passageway for nasal breathing through the naso-pharynx.

A still further object of the present invention is to provide an anti-snore device which prevents oral breathing by obstructing the flow of air through the mouth, holds the tongue forwardly so as to prevent soft tissue vibration, and opens the air passageway for nasal breathing.

And still another object of this invention is to provide a novel combination anti-snore and anti-bruxism device.

These and other objects and advantages of the invention will become clear from the following description of a preferred embodiment of the invention.

BRIEF SUMMARY OF THE INVENTION

The anti-snore and anti-bruxism device of this invention is adapted for insertion into the mouth of a user with means for obstructing the oral flow of air and for holding the tongue forwardly, thereby preventing oral breathing and enlarging the internal naso-pharynx to enhance nasal breathing. In one form, the device includes a molded body portion of a size to cover the user's mouth and lips, and another portion for entry into the mouth to engage at least one of the user's upper or lower teeth or gum arches to hold the device in position and to prevent the passage of air therepast. In a second form, the device eliminates the portion thereof located outside of the user's lips, and the portion located within the user's mouth is shaped somewhat differently and in a manner that facilitates molding. In both forms a tongue-receiving socket with a closed forward end extends rearwardly from and is provided by the body portion, the rear end of the socket being open and sized and shaped to receive a part of the forward end of the user's tongue. When operatively positioned within the mouth, the user creates a negative pressure within the socket by applying gentle suction, thereby effecting a holding by the socket of a portion of the tongue within the socket. The position of the tongue, when so secured, is to be pulled forwardly of its normal resting position behind the lower teeth. The remainder of the body of the tongue, when held forwardly of its normal proximity to the soft palate, the uvula and the posterior pharyngeal wall, provides an increase in size of the nasal air passageway. Because the devices are molded for removal cooperation with the upper and lower dental arches, relative jaw movement is effectively precluded, and nocturnal tooth grinding is prevented.

DETAILED DESCRIPTION OF THE INVENTION

Figure 1:
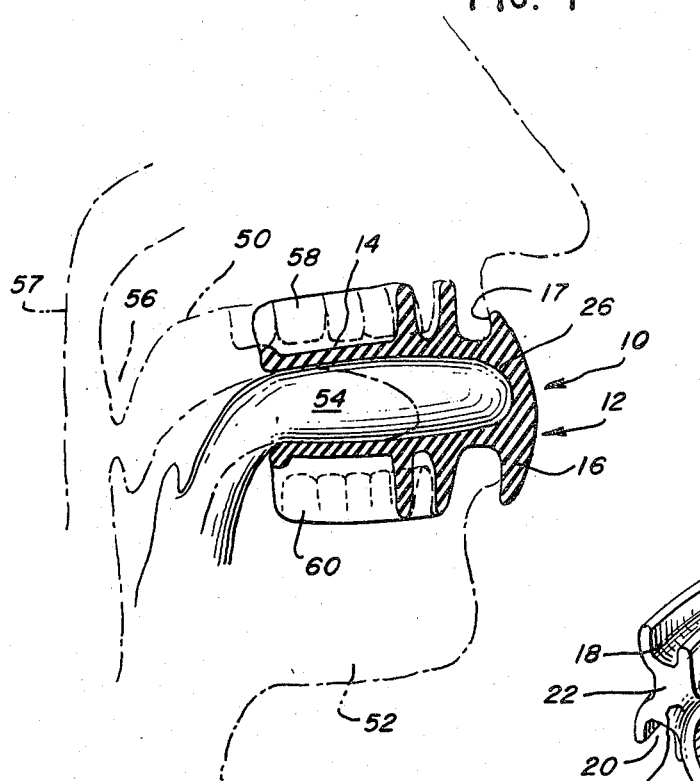
FIG. 1 is a vertical, cross-sectional view, along the longitudinal axis, of line 1—1 of FIG. 2, of a first form of the anti-snoring and anti-bruxism device of the present invention, illustrating the device operatively positioned in the mouth of a user.
Figure 2:
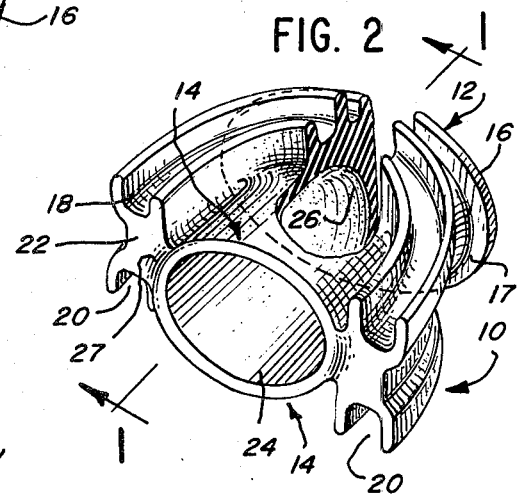
FIG. 2 is a perspective view of the embodiment of the invention shown in FIG. 1, the embodiment including upper and lower dental-engaging arches in the anti-snoring device, and with a forward portion of the device partially cut away to provide illustration of the invention's features.

Referring now to the drawings, one form of the anti-snoring and anti-tooth-grinding device of this invention is shown generally as 10 in FIGS. 1 and 2. This specific device comprises a means 12 for preventing the flow of air through the mouth and an elongated tongue-receiving socket 14 for opening the nasal breathing passage.

FIG. 1 depicts the usual anatomical structure of the mouth of a user of the device of the present invention. The mouth includes an upper jaw 50, a lower jaw 52, a tongue 54, the soft palate or musculus uvulae 56 handing downwardly approximate the base of the tongue, the posterior pharyngeal wall 57, and the upper and lower dental arches comprising upper and lower gums or upper and lower natural teeth 58 and 60.

Although the drawings depict a device adapted for mounting about the teeth of a user, it should be apparent that the device is readily modifiable for use by people having few if any natural teeth. For such usage, the U-shaped trough is widened so as to fit the upper and/or lower gums of the dental arches.

The body means 12 includes an enlarged and rearwardly curved front plate 16 adapted to be placed over the exterior surface of the lips so as to completely cover the mouth opening. Also formed as part of the body means 12 is an upper U-shaped trough 18 and a lower U-shaped trough 20 molded to closely conform to the configuration of the upper and lower dental arches and adapted to receive either the gums or the natural teeth 58 and 60 of a user. The upper and lower teeth/gum-receiving, U-shaped, troughs 18 and 20 are spaced apart by a central web 22. Both troughs 18 and 20 and the web 22 are generally semicircular in shape to substantially conform to the anatomical shape of the upper and lower dental arches.

The tongue-receiving socket 14 is an elongated element molded integrally with the body means so as to form an oppositely disposed, closed end 26 extending from the rear wall 17 or the curved plate 16 and an open end 24 extending internally of the mouth and sized to accept the tongue of a user therein. As seen in FIG. 2, the socket 14 may be stabilized by diametrically arranged molded portions 27 extending between the exterior of socket 14 and adjacent exterior portions of an arch 18 or web 22.

Figure 3:
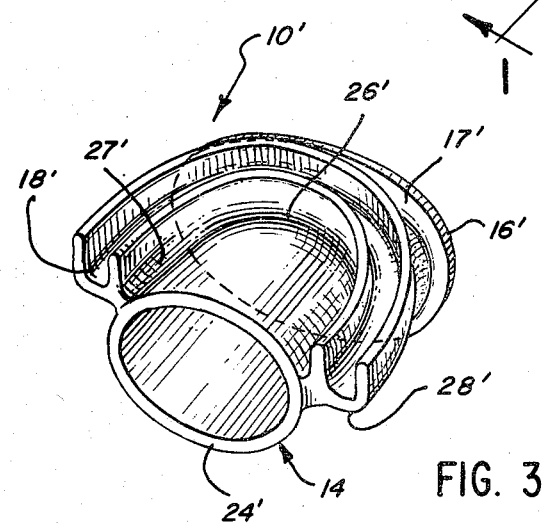
FIG. 3 is a perspective view of a second embodiment of an anti-snoring device of the present invention, the embodiment including an upper dental arch-securing trough.

FIG. 3 represents a simplified embodiment 10' of the anti-snoring and anti-bruxism device of the present invention disclosed in FIGS. 1 and 2, and wherein identical numbers represent substantially identical parts of the FIGS. 1–2 embodiment. A tongue-receiving socket 14' is molded integrally with an upper U-shaped trough 18' and a curved front plate 16'. The socket 14' includes a forward, closed end 26' and an open, rear end 24'. In this form, the device 10' may be inserted into the mouth of a user to engage the upper dental arch with the lower surface 28' of the trough resting upon the top of the lower dental arch. The lower trough surface 28' assists in clamping the device 10' between the upper and lower jaws so that the socket 14' will be positioned to hold the tongue 54 forward of its normal position. The main securing force is furnished by the close conformity between the molded upper trough 18' and the upper gum or teeth 58 forming the upper dental arch.

This embodiment permits some voluntary movement of the lower jaw 52 relative to the upper jaw 50 so as to allow swallowing of accumulated saliva. Further, the rigid constraints of the double trough embodiment are absent, thereby alleviating the anxiety which complete enclosure might cause some people. After experiencing this less restrictive model, the user may wish to acquire the more inclusive double trough device 10 or even proceed to a custom-built model.

Although the device could best be fitted by a dentist trained in the art of fabricating similar oral prostheses for the replacement of natural dental structures, a similar device could be produced in several sizes and shaped for over-the-counter sales at considerably less expense. An exact reproduction is not necessary, given the adaptability of the soft and yielding tongue to accommodate itself to a space provided for it.

Figure 4:
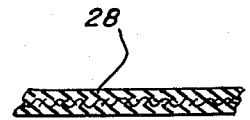
FIG. 4 is a cross-sectional view of a portion of the molded plastic wall of the anti-snoring device illustrating the use of an embedded layer of wire mesh for strength and shape maintenance.

The device is preferably molded of any well-known synthetic plastic resin that displays properties that render the plastic more pliable if warmed to a relatively low temperature above body temperature, with solidification occurring as it cools to body temperature. One such resin is ethylene vinyl acetate. Alternatively, the troughs could be lined with a yielding rubber or plastic material so that biting down would provide sufficient gripping power to securedlyhold the device. If desired, an oxidation-resistant wire mesh 28 may be embedded with the plastic resin for enhancing structural strength, rigidity and durability (see FIG. 4).

It should be appreciated that a single troughed design for engaging the lower dental arch is also within the scope of this invention.

OPERATION

In use, the device 10 is placed in hot water or otherwise warmed to a temperature above body temperature wherein the plastic becomes pliable, but which will not burn or otherwise harm the oral tissue which it later is to contact. The device 10 is then positioned in the mouth of the user such that the upper U-shaped trough 18 receives the upper teeth 58 and the lower U-shaped trough 20 receives the lower teeth 60. The user, by closing his jaws, bites into the troughs 18 and 20. Since the device is in its heated, pliable state, the upper and lower teeth 58 and 60 make impressions in the trough surfaces 18 and 20. The device 10 is left in position in the mouth until cooling brings about solidification after which the molded impressions operate to secure the device in operative position as seen in FIG. 1.

By means of insertion of the tongue tip and gentle suction therepast, the forward end of the tongue 54 will be drawn into the socket 14 in a substantially airtight relation, so as to be held forward of its normal resting position, thus bringing the body of the tongue also forward from its usual proximity to the soft palate 56 and the posterior pharyngeal wall 57. The front plate 16 and the upper and lower troughs 18 and 20 serve to prevent the oral flow of air, while the socket 14, by maintaining the tongue in a forward position, opens the nasal breathing passageway, which prevents soft tissue vibration as air passes through said passage. By restricting the jaw movement, nocturnal tooth grinding is also prevented.

The single-troughed device 10' is substantially identical in operation to the double-troughed device 10, the principal difference being that complete jaw movement is not prevented. However, oral breathing is still substantially eliminated by the curved plate 16' overlying the lips, and the single tooth-engaging trough 18' is sufficient to prevent nocturnal tooth grinding.

PREFERRED FORM OF CONSTRUCTION

Figure 5:
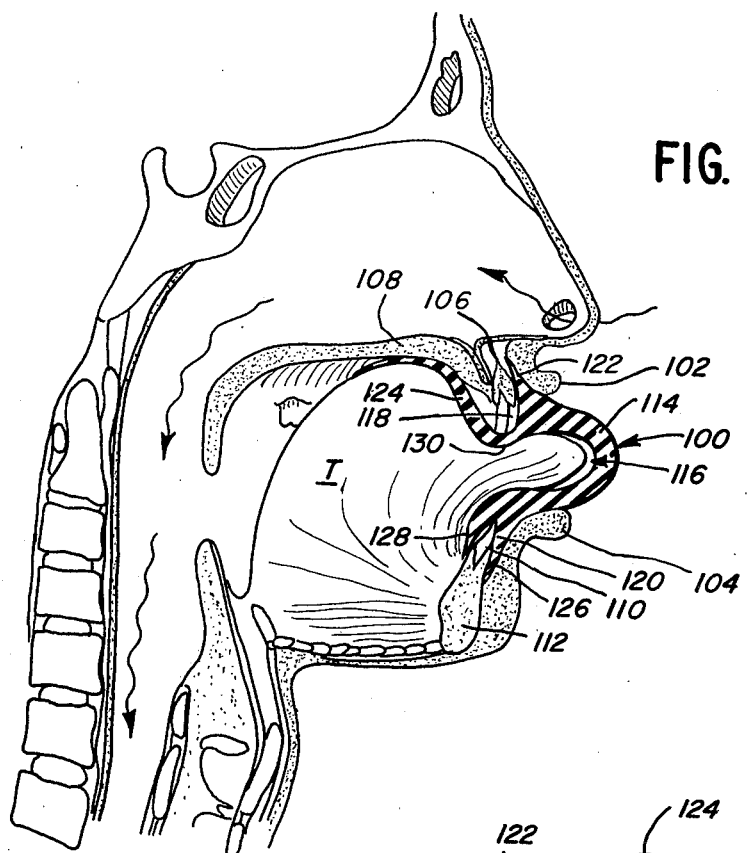
FIG. 5 is a view similar to FIG. 1 but showing an improved form of the device of this invention.
Figure 6:
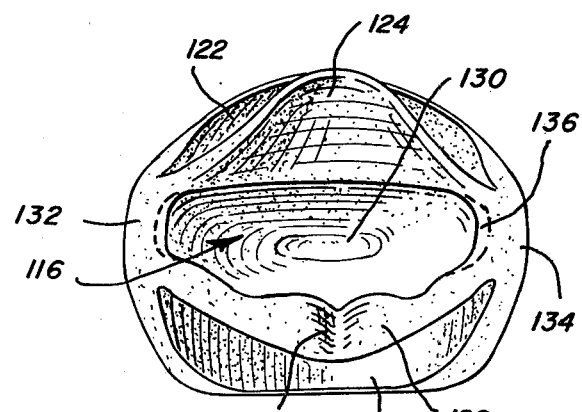
FIG. 6 is a rear elevational view of the improved form of device shown in FIG. 5.
Figure 7:
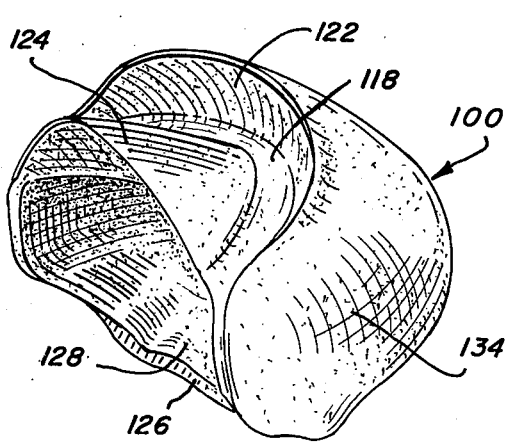
FIG. 7 is a side perspective view, somewhat from the rear, of the device of FIGS. 5 and 6.

In recent experimentation with devices of the type disclosed hereinbelow, I discovered that a simpler device could be provided for securing the anti-snore and anti-bruxism advantages sought. FIGS. 5-7 disclose the improved device discovered by my research.

In FIG. 5, the improved device is a unitary, formed body, generally indicated at 100 and is shown mounted in the mouth of a user. For purposes of reference, the user's upper lip is shown at 102, the lower lip at 104, the upper tooth arch at 106, the upper, or hard palate at 108, the lower tooth arch at 110 extending upwardly from lower gum 112, and the tongue is generally indicated at "T" as shown in FIG. 5.

The imperforate air flow preventing means of device 100 is of a size and shape to have a forward and outer portion 114 to protrude between the user's lips 102 and 104. The device 100 is also shaped to provide an elongated, rearward, socket means, generally 116, having a forward closed end and a rearward open end into which a portion of tongue "T" is inserted.

The vertical axial cross-section illustration in FIG. 5 discloses that the exterior of the air flow preventing means 100 is shaped to provide therein upper and lower recesses that are adapted for receiving thereinto forward portions of said upper and lower dental arches which engage that device 100 to hold same in position and to limit rearward movement thereof further into the mouth of the user. The device 100 may be removed from the mouth of the user by spreading the jaws and disengaging same from the teeth and then pulling the device forwardly out of the mouth.

The teeth-receiving upper recess is indicated at 118 and the teeth-receiving lower recess is indicated at 120. Bounding the forward portion of said upper recess 118 is a flange 122 that fits between the upper lip 102 and the forward portion of the upper teeth and gum arch. Rearwardly of said forward portion of the upper teeth arch 106 is an upper shelf 124, that is shaped to bound a rearward portion of the elongated socket means 116 and to lie closely adjacent in spaced relation to, or even directly abutting, the upper hard palate 108. The portions of the body 100 that bounds said lower recess 120 include a forward flange 126 which fits between the lower lip 104 and the forward portion of the lower tooth arch 110, and a lower shelf 128. The upper shelf 124 extends rearwardly into the mouth of the user a greater distance than the lower shelf 128.

With respect to the elongated socket means 116 defined in body 100, it is preferred that there be a constriction therein whose location is indicated generally at 130 that is spaced axially between the front and rear ends of said socket means 116 and closer to the front end of the socket means than to the rearmost end of the socket means. The purpose of this constriction 130 is to generally duplicate a constricted neck of an opening, such as is found in the mouth of a soft drink bottle, so that when air has been evacuated from the forward portion of the socket means 116, only the tip of the tongue enters into the portion of socket 116 forwardly of constriction 130 and is held by the constriction or neck 130 in that position, thus drawing the tongue forwardly to the position seen in FIG. 5.

With respect to the actual device produced by my experimentation, FIGS. 6 and 7 illustrate generally the type of shape that the exterior of the air flow preventing means will take. Thus, in FIG. 6 it will be seen from the rear view that the shape is generally ovate in elevation, corresponding with the fact that a person's mouth is laterally elongated relative to the normal vertical spacing of the lips. Also, the upper flange 122 and upper shelf 124 are of varying peripheral shape selected to perform their respective functions. The upper flange 122 merges with the side portions 132 and 134 that are selected to be of a dimension to engage the buccal portions of the mouth. The rearward portion of the socket means 116 has an ovate shape that is laterally elongated and vertically reduced as seen at 136 with a central crease 138 in the lower wall to accommodate the structure of the bottom of the tongue T. The constriction seen in FIG. 6 is indicated generally at 130 and is located forwardly within the elongated socket means 116. The upper shelf 124 is of sufficient width to comfortably accommodate the upper tooth arch 106.

FIG. 7 is a side perspective view taken partly from the rear and illustrates more clearly both the nature of the upper recess 118, for receiving the forward portion of the upper tooth arch 106, and the relative proportioning and appearance of the upper flange 122 and upper shelf 124. The upper shelf 124 is not required to contact upper palate 108 or the upper gum portion of the arch 106, but does provide an inner surface that makes suction contact with the tongue.

The forward flange 126 is thinned or tapered to provide a comfortable fit with and against the gum of the lower tooth arch 110. The height of the side portions 132 and 134 (seen in FIG. 6) is selected so as to fit comfortably between the upper and lower teeth and to provide at their inner surfaces a seal with the tongue.

The device 100 cannot be used by a person that is unable to breathe freely through his nasal passageways. However, use of the device has exhibited initial promise as a prosthesis for aiding in avoidance of, or obviating, problems associated with sleep apnea in elderly persons, wherein cases have been reported where the person's tongue is swallowed, leading to suffocation.

While the protrusion of the body 100 from between the lips 102 and 104 may be exaggerated in FIG. 5 for purposes of illustration, I have determined that the length of the socket means 116 and thickness of wall body 100 at the forward end, extending forwardly of the tooth line, need not be in excess of only about ⅝".

While particular forms of my invention have been disclosed and described, it will be understood that the invention may be utilized in other forms and for other purposes, so that the purpose of the appended claims is to cover all such forms of devices not disclosed but which embody the invention disclosed herein.

As noted earlier above, the body 100 is preferably formed from a synthetic plastic resin that displays the property that renders the plastic more pliable when warmed to a relatively low temperture above body temperature, with solidification occurring as the resin is cooled to body temperature. One such resin is ethylene vinyl acetate.

What is claimed and desired to be secured by Letters Patent of the United States is:

1. A device for treatment of a condition of snoring, or bruxism, or for avoidance of sleep apnea comprising, in combination:

imperforate air flow preventing means of a size and shape to be removably positioned in the user's mouth, to be held therein by the user's lips when normally biased toward their closed attitude, for preventing the flow of air through the mouth of a user, said air flow preventing means being shaped to provide a portion that fits between the user's upper and lower dental arches, and being formed to provide at least one trough thereon that is adapted to closely conform to the configuration of one of said dental arches to receive therein either the user's gum or natural teeth, with said trough providing a wall that is adapted to be located between said dental arch and the inner surface of at least one of the user's upper and lower lips, and a tongue engageable means that is shaped to define a rearwardly opening, elongated socket means, the socket means having a forward closed end and a rearward open end that is of a size, shape and location for receiving a portion of the tongue of a user thereinto to effect an airtight seal therewith when air has been sucked from the forward portion of said socket means past the tongue, such that negative pressure, created by the suction, will serve to hold the portion of the tongue in the socket, whereby the tongue is then held forwardly of its usual resting position behind the lower teeth, thereby bringing the remainder of the body of the tongue forward from its normal proximity to the soft palate, the uvula and the posterior pharyngeal wall, to form and maintain an airway of increased size through the nasopharynx and the oropharynx.

2. A device as in claim 1 wherein the exterior of the air flow preventing means is shaped to provide upper and lower troughs adapted for receiving thereinto front portions of the upper and lower dental arches to engage same and to limit rearward movement of the device into the mouth of the user.

3. A device for treatment of a condition of snoring, or bruxism, or for avoidance of sleep apnea comprising, in combination:

imperforate air flow preventing means of a size and shape to be removably positioned in the user's mouth, to be held therein by the user's lips when normally biased toward their closed attitude, for preventing the flow of air through the mouth of a user, said air flow preventing means being shaped to provide a tongue engageable means that is shaped to define a rearwardly opening, elongated socket means, the socket means having a forward closed end and a rearward open end that is of a size, shape and location for receiving a portion of the tongue of a user thereinto to effect an airtight seal therewith when air has been sucked from the forward portion of said socket means past the tongue, such that negative pressure, created by the suction, will serve to hold the portion of the tongue in the socket, whereby the tongue is then held forwardly of its usual resting position behind the lower teeth, thereby bringing the remainder of the body of the tongue forward from its normal proximity to the soft palate, the uvula and the posterior pharyngeal wall, to form and maintain an airway of increased size through the nasopharynx and the oropharynx; the exterior of said air flow preventing means being shaped to provide upper and lower recess means adapted for receiving thereinto front portions of the upper and lower dental arches to engage same and to limit rearward movement of the device into the mouth of the user; and the portions of the respective upper and lower recess means extending rearwardly of said upper and lower dental arches providing spaced upper and lower shelves of different lengths with the upper shelf extending rearwardly into the mouth of a user a greater distance than the corresponding lower shelf that extends rearwardly of the lower recess means, and said upper shelf being adapted to lie closely adjacent to, or even directly abutting, the upper palate of a user's mouth.

4. A device as in claim 1 or claim 3 wherein the elongated socket means includes a constriction therein spaced axially between the front and rear ends of the socket means and closer to the front end of the socket means.

5. A device as in claim 1 or claim 3 wherein the device is integrally molded of a synthetic plastic resin material that has the property that renders the plastic material more pliable when warmed to a temperature above body temperature, but which solidifies when cooled to body temperature.

6. A device as in claim 5 wherein the synthetic plastic resin material is ethylene vinyl acetate.

* * * * *